United States Patent [19]

Suzuki

[11] 4,340,757
[45] Jul. 20, 1982

[54] PROCESS FOR THE PREPARATION OF 2,6-DIALKYLANILINE FROM BROMINATED DIALKYL T-BUTYLBENZENE

[75] Inventor: Shigeto Suzuki, San Francisco, Calif.

[73] Assignee: Chevron Research Company, San Francisco, Calif.

[21] Appl. No.: 280,440

[22] Filed: Jul. 6, 1981

[51] Int. Cl.$^3$ .................................................. C07C 85/04
[52] U.S. Cl. ...................................... 564/407; 564/305; 564/437
[58] Field of Search ................ 564/305, 407; 570/206

[56] References Cited

U.S. PATENT DOCUMENTS

| | | | |
|---|---|---|---|
| 1,607,824 | 11/1926 | Hale et al. | 564/407 |
| 1,775,360 | 9/1930 | Williams | 564/407 |
| 1,935,515 | 11/1933 | Mills | 564/407 |
| 2,062,349 | 12/1936 | Calcott et al. | 564/407 |
| 3,057,922 | 10/1962 | Luvisi et al. | 564/407 |

FOREIGN PATENT DOCUMENTS

| | | | |
|---|---|---|---|
| 2436111 | 2/1975 | Fed. Rep. of Germany | 564/407 |
| 51-59824 | 5/1976 | Japan | 564/407 |

*Primary Examiner*—John Doll
*Attorney, Agent, or Firm*—J. A. Buchanan, Jr.; T. G. DeJonghe; C. J. Caroli

[57] ABSTRACT

A process for the preparation of 2,6-dialkylaniline which comprises the reaction of 1,3-dialkyl-5-tertiary-butylbenzene with molecular bromine to form 2-bromo-1,3-dialkyl-5-tertiary-butylbenzene, which is subsequently reacted with 1,3-dialkylbenzene in the presence of hydrogen fluoride to form a mixture of 2-bromo-1,3-dialkylbenzene and 1,3-dialkyl-5-tertiary-butylbenzene, which is then reacted with ammonia in the presence of a catalytic amount of cuprous halide.

15 Claims, No Drawings

PROCESS FOR THE PREPARATION OF 2,6-DIALKYLANILINE FROM BROMINATED DIALKYL T-BUTYLBENZENE

BACKGROUND OF THE INVENTION

This invention is concerned with an improved process for the preparation of 2,6-dialkylaniline which comprises the reaction of 1,3-dialkyl-5-tertiary-butylbenzene with molecular bromine to form 2-bromo-1,3-dialkyl-5-tertiary-butylbenzene, which is subsequently reacted with 1,3-dialkylbenzene in the presence of hydrogen fluoride to form a mixture of 2-bromo-1,3-dialkylbenzene and 1,3-dialkyl-5-tertiary-butylbenzene, which is then reacted with ammonia in the presence of a catalytic amount of cuprous halide.

One method of preparing 2,6-dialkylaniline is by the amination of hydroxy aromatics. U.S. Pat. No. 3,931,298 describes a process for the preparation of aromatic amines by the reaction of hydroxy-substituted aromatic compounds with ammonia in the presence of a catalytic amount of a cyclohexanone and in contact with a hydrogen transfer catalyst.

U.S. Pat. No. 3,960,962 describes a related process wherein aromatic hydroxy compounds are converted to the corresponding aromatic amine by reaction with ammonia in the presence of a cyclohexanone promoter and a catalyst comprising metallic palladium bonded to a phosphinated polystyrene resin.

In U.S. Pat. No. 3,965,182 aromatic amines are made by reacting a phenol with aluminum nitride and either ammonia or a primary or secondary amine.

U.S. Pat. No. 3,801,642 is concerned with a process for replacing an aromatic hydroxyl group with an amine group by forming a metal aryloxide from the corresponding aromatic hydroxy compound and reacting the metal aryloxide with ammonia or a primary or secondary amine in the presence of a Friedel-Crafts catalyst.

U.S. Pat. No. 4,125,560 describes the direct amination of phenols with amines by the ammonolysis of phenols in a liquid phase under pressure with an aqueous ammonia solution containing a catalytic amount of an ammonium salt.

U.S. Pat. No. 3,219,704 describes the preparation of aromatic amines by the condensation of six-membered alicyclic ketones and ammonia compounds with a dehydrogenation catalyst, wherein the molar portion of the ketone is at least substantially equal to the ammonia compound.

In U.S. Pat. No. 3,442,950 aminated benzenes are prepared by catalytically reacting a cyclohexanol with an aminating agent. When cyclohexanone is present in the cyclohexanol component, the reaction is initiated in the presence of one mole of hydrogen per mole of cyclohexanone.

Dialkylanilines, and in particular 2,6-dialkylanilines, are useful intermediates for a variety of compounds having herbicidal and fungicidal activity.

SUMMARY OF THE INVENTION

It has now been found that 2,6-dialkylanilines, wherein each alkyl group is a straight chain of 1-4 carbon atoms, may be prepared in high yield by a process which comprises:
 (a) contacting 1,3-dialkyl-5-tertiary-butylbenzene wherein each alkyl group is a straight chain of 1-4 carbon atoms with molecular bromine at a temperature of from about −10° C. to about 80° C. to form 2-bromo-1,3-dialkyl-5-tertiary-butylbenzene;
 (b) contacting the 2-bromo-1,3-dialkyl-5-tertiary-butylbenzene with 1,3-dialkylbenzene wherein each alkyl group is a straight chain of 1-4 carbon atoms in the presence of hydrogen fluoride at a temperature of from about −10° C. to about 80° C. and a pressure of from about 5 psig to about 300 psig to form 2-bromo-1,3-dialkylbenzene and 1,3-dialkyl-5-tertiary-butylbenzene;
 (c) contacting the 2-bromo-1,3-dialkylbenzene and 1,3-dialkyl-5-tertiary-butylbenzene formed in (b) with ammonia in the presence of a catalytic amount of cuprous halide at a temperature of from about 150° C. to about 300° C. to thereby obtain a reaction mixture comprising 2,6-dialkylaniline and 1,3-dialkyl-5-tertiary-butylbenzene; and
 (d) separating 2,6-dialkylaniline from the reaction mixture.

In a preferred embodiment of the present invention, the 1,3-dialkyl-5-tertiary-butylbenzene produced in step (b) above is separated from the reaction mixture of step (c) and recycled back to step (a).

Preferable 2,6-dialkylanilines prepared by this method include those wherein each alkyl group independently contains 1-2 carbon atoms, such as 2-methyl-6-ethylaniline and 2,6-diethylaniline. Most preferably, the 2,6-dialkylaniline is 2,6-dimethylaniline.

1,3-Dialkyl-5-tertiary-butylbenzenes are used as starting materials. Preferable 1,3-dialkyl-5-tertiary-butylbenzenes include those wherein each alkyl group independently is methyl or ethyl. Especially preferred is 1,3-dimethyl-5-tertiary-butylbenzene. The 1,3-dialkyl-5-tertiary-butylbenzenes may be prepared by known processes, such as the reaction of 1,3-dialkylbenzene with isobutene in the presence of hydrogen fluoride as described, for example, in U.S. Pat. No. 2,860,169 to Schlatter.

The 1,3-dialkyl-5-tertiary-butylbenzene is reacted with molecular bromine at a temperature from about −10° C. to about 80° C., preferably from about 0° C. to about 40° C., to form the desired 2-bromo-1,3-dialkyl-5-tertiary-butylbenzene. A catalytic amount of ferric halide may optionally be added to suppress formation of the 4-bromo isomer. The reaction may be carried out with or without a solvent. When a solvent is used, it should be an organic solvent which is inert to reaction with 1,3-dialkyl-5-tertiary-butylbenzene and with molecular bromine. Examples of suitable solvents include dichloromethane, chloroform, dichloroethane, tetrachloroethane, 1,2-dichlorobenzene, nitrobenzene, carbon disulfide and hexane. A preferred solvent is carbon tetrachloride. The reaction is usually conducted at atmospheric pressure. Generally, about 0.1 to 1.1 moles, preferably 0.8 to 1 mole, of molecular bromine are utilized per mole of 1,3-dialkyl-5-tertiary-butylbenzene. The 2-bromo-1,3-dialkyl-5-tertiary-butylbenzene is generally purified by conventional procedures and is obtained in near quantitative yield.

The 2-bromo-1,3-dialkyl-5-tertiary-butylbenzene thus formed is reacted with 1,3-dialkylbenzene in the presence of a separate liquid hydrogen fluoride phase as a catalyst. Preferred 1,3-dialkylbenzenes include those wherein each alkyl group independently is methyl or ethyl. An especially preferred 1,3-dialkylbenzene is 1,3-dimethylbenzene or meta-xylene. The reaction may be carried out without a solvent at a temperature from about −10° C. to about 80° C., preferably from about 30° C. to about 60° C., and a pressure from about 5 psig to about 300 psig, preferably from about 20 psig to about 100 psig. Generally about 0.1 to 10, and preferably 0.2 to 4, moles of 1,3-dialkylbenzene are utilized per mole of 2-bromo-1,3-dialkyl-5-tertiary-butylbenzene. The reaction is normally run in the presence of about 5 to 30 weight percent of liquid hydrogen fluoride as a separate phase. The reaction proceeds to provide a mixture of 2-bromo-1,3-dialkylbenzene and 1,3-dialkyl-5-tertiary-butylbenzene in about a one to one molar ratio.

The mixture of 2-bromo-1,3-dialkylbenzene and 1,3-dialkyl-5-tertiary-butylbenzene thus formed is not readily separable by fractional distillation and is therefore subjected to the successive amination of the 2-bromo-1,3-dialkylbenzene without prior separation and purification.

The amination of the 2-bromo-1,3-dialkylbenzene is carried out by reacting the mixture of 2-bromo-1,3-dialkylbenzene and 1,3-dialkyl-5-tertiary-butylbenzene with ammonia in the presence of a cuprous halide catalyst. The reaction may be carried out at a temperature from about 150° C. to about 300° C., preferably from about 180° C. to about 260° C. The reaction pressure is normally atmospheric. The preferred cuprous halide catalyst is cuprous bromide.

The amination reaction may be run in either aqueous ammonia or anhydrous ammonia. Since the use of aqueous ammonia may result in the formation of phenolic by-products, such as 2,6-xylenol, the use of anhydrous ammonia is preferred. When run in anhydrous ammonia, the reaction is normally carried out in the presence of an organic solvent. Suitable organic solvents include alcohols, such as ethanol, aromatic hydrocarbons, such as toluene, aromatic heterocyclic compounds, such as pyridine, ethers, such as diethyl ether, tetrahydrofuran and the like, and organic sulfones, such as perhydrothiophene-1,1-dioxide.

Amide solvents, such as acetamide or pyrrolidone, are preferred. However, formamide and dimethyl formamide have been found not to be suitable as solvents. Generally, about 1 to 30 moles, and preferably 3 to 15 moles, of ammonia are utilized per mole of 2-bromo-1,3-dialkylbenzene.

The reaction proceeds to provide a mixture of 2,6-dialkylaniline and 1,3-dialkyl-5-tertiary-butylbenzene. The 2,6-dialkylaniline product is separated from the reaction mixture and purified by conventional procedures, such as distillation. The 1,3-dialkyl-5-tertiary-butylbenzene, originally formed in the preceding transalkylation reaction, can also readily be separated from the reaction mixture by conventional methods and recycled back to the initial stage of the process as regenerated starting material.

The following examples are provided to illustrate the invention in accordance with the principles of this invention but are not to be construed as limiting the invention in any way except as indicated by the appended claims.

EXAMPLE 1

A 100 ml. 3-necked flask equipped with a magnetic stirrer, thermometer, reflux condenser and a rubber-covered side arm was charged with 16.2 grams (0.1 mole) of 1,3-dimethyl-5-t-butylbenzene and 1 gram (0.006 mole) of anhydrous ferric chloride. This charge was cooled to 0° C. The mixture was stirred while 5.98 grams (0.037 mole) of bromine was slowly added via a syringe over a period of about 4 minutes. The temperature rose to 15° C. Then the mixture was stirred for an additional 100 minutes as the temperature rose to 24° C.

At the end of this time, the organic layer was washed first with 20% aqueous HCl and then with concentrated HCl, and finally with salt water. After drying, the product mixture was analyzed by gas chromatography. This analysis showed a 36% conversion to brominated products. The ratio of 2-bromo-1,3-dimethyl-5-t-butylbenzene to 4-bromo-1,3-dimethyl-5-t-butylbenzene was 98.7 to 1.3.

Other runs were carried out in a similar fashion to give the results shown in Table I.

TABLE I

| | | | BROMINATION OF DMBB[1] | | | | | | | |
|---|---|---|---|---|---|---|---|---|---|---|
| Ex. No. | DMBB (Moles) | Bromine (Moles) | Solvent Kind | Quantity[2] | FeCl$_3$ (Wt. %)[3] | Time (Min.)[4] | Temp. (°C.) | Conv. (Mole %) | Selectivity[5] 2-Br | 4-Br |
| 2 | 1.0 | 0.3 | None | — | 0.6 | 18 | 5–18 | 32 | 99 | 1 |
| 3 | 0.05 | 0.05 | CCl$_4$ | 2.5 | 0 | 120 | 10–21 | 98 | 94 | 6 |
| 4 | 1.21 | 1.21 | CCl$_4$ | 0.8 | 0 | 90 | 10–20 | 99.5 | 95 | 5 |
| 5 | 0.12 | 0.12 | CCl$_4$ | 0.8 | 1.0 | 20 | 9–15 | 99+ | 99.5 | 0.5 |

[1]DMBB = 1,3-Dimethyl-5-t-butylbenzene
[2]Weight factor of DMBB
[3]Based on DMBB
[4]After Bromine addition completed
[5]2-Br = 2-Bromo-1,3-dimethyl-5-t-butylbenzene; 4-Br = 4-Bromo-1,3-dimethyl-5-t-butylbenzene.

Examples 1 and 2 show that a solvent is not essential to this reaction. However, in the presence of a solvent, conversions of 1,3-dimethyl-5-t-butylbenzene can be increased to 100% without undue loss to overbromination.

Examples 1, 2 and 5 as compared to Examples 3 and 4 show that ferric chloride in catalytic amounts suppresses the formation of the undesired 4-bromo-1,3-dimethyl-5-t-butylbenzene.

In Examples 2 and 4, pure 2-bromo-1,3-dimethyl-5-t-butylbenzene was separated from the 4-isomer by crystallization from absolute ethanol.

Examples 1 to 5 show that 2-bromo-1,3-dimethyl-5-t-butylbenzene can be obtained in near quantitative yield in a short reaction time, and under mild conditions by adding bromine to 1,3-dimethyl-5-t-butylbenzene.

EXAMPLE 6

A plastic bottle having a 25 ml. capacity was charged with 2.42 grams (0.01 mole) of 2-bromo-1,3-dimethyl-5-t-butylbenzene, 4.12 grams (0.04 mole) of metaxylene and 4.0 grams of liquid HF. The contents were stirred at 0° C. for 2.5 hours. Analysis of the crude product showed about 10% conversion of 2-bromo-1,3-dimethyl-5-t-butylbenzene to give equal molar amounts of 1,3-dimethyl-5-t-butylbenzene and 2-bromo-1,3-dimethylbenzene.

EXAMPLE 7

A 200 ml. metal reactor equipped with a stirrer and a pressure gauge and at a temperature of 0° C. was charged with 9.68 grams (0.04 mole) of 2-bromo-1,3-dimethyl-5-t-butylbenzene, 16.48 grams (0.16 mole) of meta-xylene and 8.0 grams (0.4 mole) of liquid HF. The reactor was sealed and heated to 45° C. After 1 hour at this temperature, nitrogen was added to give a pressure of 40 psig. The reactor was heated to 50° C., at which temperature the pressure was 50 psig. It was held there for 60 minutes. Then an aliquot was removed for analysis. Heating at 50° C. was continued for another 70 minutes, when a second analytical sample was removed.

The two analytical samples were analyzed using a gas chromatograph. Both showed essentially equal amounts of 1,3-dimethyl-5-t-butylbenzene and 2-bromo-1,3-dimethylbenzene. Conversion of 2-bromo-1,3-dimethyl-5-t-butylbenzene was 88% in the first sample and 89% in the second.

Other transalkylation runs were carried out in a similar manner. These examples are given in Table II.

terial. The remainder, after evaporation of the ether, weighed 375 grams. This was distilled at 40 mm Hg to give separate fractions of meta-xylene, 2-bromo-1,3-dimethyl-5-t-butylbenzene and a mixed fraction composed of 1,3-dimethyl-5-t-butylbenzene and 2-bromo-1,3,-dimethylbenzene.

The mixed fraction is utilized in the final step of the process wherein the bromine is replaced by an amino group. In that reaction, the 1,3-dimethyl-5-t-butylbenzene acts as an inert diluent. The meta-xylene fraction and the 2-bromo-1,3-dimethyl-5-t-butylbenzene fraction are recycled to the butyl transfer reaction.

EXAMPLE 10

A microbomb of 15 ml. capacity was charged with 1.85 grams (0.01 mole) of 2-bromo-1,3-dimethylbenzene and 3.6 grams (0.06 mole) of 28% ammonium hydroxide. The reactor was sealed and heated at 200° C. for 4 hours. At the end of this time, the reactor was cooled, the contents were removed and then the bomb was washed with 5 ml. of water and 10 ml. of ether. All washes were combined with the crude reaction product. Then 0.01 mole of sodium hydroxide in 10% aqueous solution was added. The ether layer was separated

TABLE II
DEBUTYLIZATION OF 2-BROMO-1,3-DIMETHYL-5-t-BUTYLBENZENE

| Ex. No. | 2-Br[1] (Moles) | M—X (Moles) | HF (Grams) | Time (Min.) | Temp. (°C.) | Pressure (psig) | Conversion[2] (Mole %) |
|---|---|---|---|---|---|---|---|
| 8 | 0.15 | 0.30 | 8 | 120 | 50 | 45 | 48 |
|   |      |      |   | 240 |    |    | 61 |
|   |      |      |   | 360 |    |    | 65 |
| 9 | 0.8 | 2.0 | 140 | 240 | 60 | 70 | 85 |

[1] 2-Bromo-1,3-dimethyl-5-t-butylbenzene
[2] Conversion of 2-bromo-1,3-dimethyl-5-t-butylbenzene into approximately equimolar quantities of 2-bromo-1,3-dimethylbenzene and 1,3-dimethyl-5-t-butylbenzene with essentially no other by-products The crude product of Example 9 (Table II) was cooled to less than 0° C. and then poured onto ice. The aqueous HF phase was separated from the organic phase with the aid of added ether. The organic phase was filtered to remove a small amount of insoluble maand analyzed by gas chromatography. Conversion to 2-amino-1,3-dimethylbenzene was 0.6%, but all product was the desired 2,6-dimethylaniline.

Other runs were carried out in a similar manner. The results are summarized in Table III.

TABLE III
AMINATION OF 2-BROMO-1,3-DIMETHYLBENZENE

| Ex. No. | BMX[1] (Moles) | NH₃, 28% aq. (Moles) | Catalyst Kind | Catalyst Qty[2] (Wt. %) | Solvent Kind | Solvent Qty (Wt. %) | Temp. (°C.) | Time (Hrs.) | Conv.[3] (Mole %) | Select.[4] (Mole %) |
|---|---|---|---|---|---|---|---|---|---|---|
| 11 | 0.01 | 0.06 | Cu₂Cl₂ | 5 | None | — | 200 | 4 | 5.5 | 75 |
| 12 | 0.01 | 0.06 | None | — | None | — | 250 | 4 | 14 | 56 |
| 13 | 0.01 | 0.06 | Cu₂Cl₂ | 5 | None | — | 250 | 4 | 53 | 63 |
| 14 | 0.01 | 0.06 | TEBA[5] | 5 | None | — | 200 | 4 | 0 | — |
| 15 | 0.01 | 0.06 | TEBA | 14 | None | — | 200 | 4 | <1 | — |
| 16 | 0.01 | 0.06 | None | — | NMP[6] | 200 | 200 | 4 | 0.6 | 100 |
| 17 | 0.01 | 0.06 | Cu₂Cl₂ | 5 | NMP | 200 | 200 | 4 | 14 | 62 |

| | | NH₃, anhyd. (Moles) | | | | | | | | |
|---|---|---|---|---|---|---|---|---|---|---|
| 18 | 0.1 | 1.05 | CuBr | 31 | H₂O | 70 | 220 | 4 | 65 | 89.6 |
| 19 | 0.0065 | 0.12 | CuBr | 48 | Acetamide | 250 | 220 | 4 | 90 | 91.6 |
| 20 | 0.01 | 0.11 | CuBr / CuBr₂ | 31 / 24 | H₂O | 70 | 220 | 4 | 98+ | 66.3 |
| 21 | 0.01 | 0.128 | CuBr | 31 | Pyrrolidone | 162 | 220 | 4 | 98 | 90.3 |
| 22 | 0.01 | 0.159 | CuBr | 31 | H₂O | 70 | 220 | 4 | 99.7 | 75.3 |
| 23 | 0.01 | 0.09 | CuCl | 5 | H₂O | 70 | 220 | 4 | 41 | 56 |
| 24 | 0.01 | 0.11 | CuCl | 25 | H₂O | 70 | 220 | 4 | 99.2 | 55 |
| 25 | 0.01 | 0.1 | CuCl | 25 | NMP | 130 | 220 | 4 | 85 | 36 |
| 26 | 0.01 | 0.1 | CuI | 10 | H₂O | 70 | 220 | 4 | 67 | 78.6 |
| 27 | 0.01 | 0.12 | CuI | 10 | H₂O | 70 | 220 | 4 | 56 | 62 |

TABLE III-continued

| | | AMINATION OF 2-BROMO-1,3-DIMETHYLBENZENE | | | | | | | |
|---|---|---|---|---|---|---|---|---|---|
| | | NH₃, | Catalyst | | Solvent | | | | |
| Ex. No. | BMX[1] (Moles) | 28% aq. (Moles) | Kind | Qty[2] (Wt. %) | Kind | Qty (Wt. %) | Temp. (°C.) | Time (Hrs.) | Conv.[3] (Mole %) | Select.[4] (Mole %) |
| | | | NH₄Br | 5 | | | | | | |

[1]2-Bromo-1,3-dimethylbenzene
[2]Wt. % based on BMX
[3]Conversion of BMX
[4]Mole % of 2,6-dimethylaniline based on BMX converted
[5]Triethylbenzylammonium Bromide
[6]N-methylpyrrolidone

EXAMPLE 28

A monel autoclave of 300 ml. capacity was charged with 36.3 grams of a mixture comprising 18.5 grams (0.10 mole) of 2-bromo-1,3-dimethylbenzene and 17.8 grams (0.11 mole) of 2-bromo-1,3-dimethyl-5-t-butylbenzene as obtained from the transalkylation reaction, 18.0 grams (0.30 mole) of 28% ammonium hydroxide, 5.8 grams of cuprous bromide and 5.0 grams of calcium carbonate. The bomb was closed and 22 grams of ammonia were added through an inlet tube. The resulting mixture was heated for 4 hours at 235° C. to 245° C. After this time, the autoclave was cooled to room temperature and the ammonia was vented. The crude product was neutralized with aqueous hydrochloric acid. The crude reaction mixture was filtered. The solid material was extracted with ether and this extract was added to the crude liquid reaction mixture. The combined mixture was washed with water and then dried over magnesium sulfate. After separation from the drying agent and evaporation of the ether, there remained 27.1 grams of crude product. Analysis of this crude product showed it to contain 4.6% meta-xylene, 56.4% 1,3-dimethyl-5-t-butylbenzene, 10.6% 2-bromo-1,3-dimethylbenzene, 21.2% of 2,6-dimethylaniline and about 7% unknown products. These values indicate a 65% conversion of 2-bromo-1,3-dimethylbenzene and an 82.4% yield of the desired 2,6-dimethylaniline.

The crude product may be further purified by adding aqueous hydrochloric acid until the pH is below 3. The non-aminated materials do not dissolve and may be phase separated, optimally by adding ether or other hydrophobic solvent. The aqueous layer is then basicified which causes the 2,6-dimethylaniline to form a separate layer which can be phase separated from the aqueous base. Further purification by distillation is also possible.

I claim:
1. A process for the preparation of 2,6-dialkylaniline wherein each alkyl group is a straight chain of 1–4 carbon atoms which comprises:
   (a) contacting 1,3-dialkyl-5-tertiary-butylbenzene wherein each alkyl group is a straight chain of 1–4 carbon atoms with molecular bromine at a temperature of from about −10° C. to about 80° C. to form 2-bromo-1,3-dialkyl-5-tertiary-butylbenzene;
   (b) contacting the 2-bromo-1,3-dialkyl-5-tertiary-butylbenzene with 1,3-dialkylbenzene wherein each alkyl group is a straight chain of 1–4 carbon atoms in the presence of hydrogen fluoride at a temperature of from about −10° C. to about 80° C. and a pressure of from about 5 psig to about 300 psig to form 2-bromo-1,3-dialkylbenzene and 1,3-dialkyl-5-tertiary-butylbenzene;
   (c) contacting the 2-bromo-1,3-dialkylbenzene and 1,3-dialkyl-5-tertiary-butylbenzene formed in (b) with ammonia in the presence of a catalytic amount of cuprous halide at a temperature of from about 150° C. to about 300° C. to thereby obtain a reaction mixture comprising 2,6-dialkylaniline and 1,3-dialkyl-5-tertiary-butylbenzene; and
   (d) separating 2,6-dialkylaniline from the reaction mixture.

2. A process in accordance with claim 1, wherein the 1,3-dialkyl-5-tertiary-butylbenzene formed in (b) is separated from the reaction mixture of (c) and recycled back to (a).

3. A process in accordance with claim 1, wherein the reaction with molecular bromine takes place in the presence of a catalytic amount of ferric chloride.

4. A process in accordance with claim 1, wherein the cuprous halide is cuprous bromide.

5. A process in accordance with claim 1, wherein each alkyl group independently is methyl or ethyl.

6. A process in accordance with claim 1, wherein the 1,3-dialkyl-5-tertiary-butylbenzene is 1,3-dimethyl-5-tertiary-butylbenzene and the 1,3-dialkylbenzene is meta-xylene.

7. A process in accordance with claim 1, wherein the reaction with molecular bromine is carried out at a temperature of from about 0° C. to about 40° C.

8. A process in accordance with claim 1, wherein the reaction of 2-bromo-1,3-dialkyl-5-tertiary-butylbenzene with 1,3-dialkylbenzene is carried out at a temperature of from about 30° C. to about 60° C. and a pressure of from about 20 psig to about 100 psig.

9. A process in accordance with claim 1, wherein the reaction with ammonia is carried out at a temperature of from about 180° C. to about 260° C.

10. A process in accordance with claim 1, wherein the amination reaction is carried out with anhydrous ammonia.

11. A process in accordance with claim 1, wherein about 0.1 to 1.1 moles of molecular bromine are employed per mole of 1,3-dialkyl-5-tertiary-butylbenzene.

12. A process in accordance with claim 1, wherein about 0.1 to 10 moles of 1,3-dialkylbenzene are employed per mole of 2-bromo-1,3-dialkyl-5-tertiary-butylbenzene.

13. A process in accordance with claim 1, wherein about 1 to 30 moles of ammonia are employed per mole of 2-bromo-1,3-dialkylbenzene.

14. A process for the preparation of 2,6-dimethylaniline which comprises:
   (a) contacting 1,3-dimethyl-5-tertiary-butylbenzene with molecular bromine in the presence of a catalytic amount of ferric chloride at a temperature of from about 0° C. to 40° C. to form 2-bromo-1,3-dimethyl-5-tertiary-butylbenzene;
   (b) contacting the 2-bromo-1,3-dimethyl-5-tertiary-butylbenzene with meta-xylene in the presence of hydrogen fluoride at a temperature of from about 30° C. to about 60° C. and a pressure of from about 20 psig to about 100 psig to form 2-bromo-1,3-dimethylbenzene and 1,3-dimethyl-5-tertiary-butylbenzene;

(c) contacting the 2-bromo-1,3-dimethylbenzene and 1,3-dimethyl-5-tertiary-butylbenzene formed in (b) with ammonia in the presence of a catalytic amount of cuprous bromide at a temperature of from about 180° C. to about 260° C. to thereby obtain a reaction mixture comprising 2,6-dimethylaniline and 1,3-dimethyl-5-tertiary-butylbenzene; and (d) separating 2,6-dimethylaniline from the reaction mixture.

15. A process in accordance with claim 14, wherein the 1,3-dimethyl-5-tertiary-butylbenzene formed in (b) is separated from the reaction mixture of (c) and recycled back to (a).

* * * * *